(12) United States Patent
Schaser

(10) Patent No.: US 10,406,614 B2
(45) Date of Patent: Sep. 10, 2019

(54) SAMPLE CUTTER

(71) Applicant: Matthew Schaser, Painesville, OH (US)

(72) Inventor: Matthew Schaser, Painesville, OH (US)

( * ) Notice: Subject to any disclaimer, the term of this patent is extended or adjusted under 35 U.S.C. 154(b) by 159 days.

(21) Appl. No.: 15/068,024

(22) Filed: Mar. 11, 2016

(65) Prior Publication Data

US 2017/0259358 A1 Sep. 14, 2017

(51) Int. Cl.
| | |
|---|---|
| *B23D 55/08* | (2006.01) |
| *G01N 1/04* | (2006.01) |
| *B23D 53/00* | (2006.01) |
| *B23D 53/04* | (2006.01) |
| B23D 55/06 | (2006.01) |
| B23D 61/12 | (2006.01) |

(52) U.S. Cl.
CPC ......... *B23D 55/082* (2013.01); *B23D 53/003* (2013.01); *B23D 53/045* (2013.01); *G01N 1/04* (2013.01); *B23D 55/065* (2013.01); *B23D 61/123* (2013.01)

(58) Field of Classification Search
CPC .. B23D 53/003; B23D 53/045; B23D 55/082; B23D 53/02; B23D 53/06; B23D 61/123; B23D 61/126; B23D 57/0053; B23D 57/0061; B23D 59/006; B23D 61/185; B23D 53/04; G01N 1/04; B28D 1/30; B28D 1/08; Y10T 83/7264; B27B 13/00; B27B 5/12
See application file for complete search history.

(56) References Cited

U.S. PATENT DOCUMENTS

| 81,434 | A | * | 8/1868 | Thompson | |
|---|---|---|---|---|---|
| 619,490 | A | * | 2/1899 | Lawrence | B23D 55/082 29/DIG. 81 |
| 1,507,460 | A | * | 9/1924 | Carroll | B27B 5/12 144/24.12 |
| 2,962,752 | A | * | 12/1960 | Massengill | A22C 17/004 452/171 |
| 3,561,310 | A | * | 2/1971 | Deeks | B23D 61/123 125/21 |
| 4,558,854 | A | * | 12/1985 | Suzuki | B25B 5/107 269/93 |

FOREIGN PATENT DOCUMENTS

DE 940186 * 7/1949

OTHER PUBLICATIONS

Buckeye III Sampler Cutting System Brochure, copyright 2014, The Equity Engineering Group, Inc.
Non-Destructive Scoop Sampling, Stress Engineering Services, Inc., http://www.stress.com/capabilities/materials-engineering/field-inspection-testing/non-destructive-scoop-sampling, Jun. 10, 2016.

* cited by examiner

*Primary Examiner* — Kenneth E Peterson
*Assistant Examiner* — Liang Dong
(74) *Attorney, Agent, or Firm* — BakerHostetler

(57) ABSTRACT

A sample cutting assembly includes a base block, a saw pressure plate, an external blade guide, and an internal blade guide. The cutter can be used to conveniently remove samples for Material testing to determine serviceability or material condition. Apparatuses and techniques for using the sample cutting assembly are also disclosed.

17 Claims, 11 Drawing Sheets

SAMPLE CUTTER

TECHNICAL FIELD

The present application generally concerns cutting devices for removing samples. The disclosures herein more specifically concern cutting devices employing a supported or guided rotating sawblade.

BACKGROUND

Material testing is important to ensure the mechanical integrity of various pieces of equipment subject to harsh operating conditions and to maintain proper safety margins for continued use of the equipment. Such testing frequently requires removal of surface and/or subsurface samples of materials such as the metals comprising such equipment. Samples of sufficient size to complete standard material testing techniques are acquired according to destructive (or partially-destructive) methods whereby material is removed from the equipment rendering it inoperable. Because many types of equipment are compromised for their purposes by the material removed (in terms of, e.g., structural integrity, safety factors, loss of impermeability to fluid), such testing requires downtime and substantial repairs or decommissioning of the equipment.

In an example, pressure vessels and storage tanks degrade over time. Depending on the materials stored therein, environmental conditions, maintenance and usage cycles, and many other variables, such equipment may remain serviceable for decades, but can potentially become unsafe much sooner. While the internal and external surfaces can provide some indication of serviceability, deeper samples taken from the inside of the container are typically required to fully assess its structural integrity, e.g., tensile strength and fracture toughness. Existing techniques capable of removing adequate samples typically require at least temporary decommissioning of the pressure vessel, removal of a section of its walls, then extensive weld repair to restore the removed section if the vessel is to be brought back to service after testing is complete. Such processes are labor-intensive, expensive, slow, and cause significant downtime and waste.

Many other types of equipment constructed of metals or other materials are also unable to be tested without substantial disruption to their operation and in turn the operation of entities employing such equipment.

SUMMARY

In an embodiment, a sample cutter includes a base block having a saw end and a drive end, a saw pressure plate disposed within the base block toward the drive end of the base block, an external blade guide disposed toward the saw end of the base block, and an internal blade guide disposed toward the saw end of the base block and at least partially within the external blade guide.

In another embodiment a sample cutting apparatus includes a sample cutting assembly along with a positioning assembly mechanically coupled with the sample cutter, the positioning assembly configured to move the sample cutter toward or away from a workpiece; and a displacement assembly mechanically coupled with the positioning assembly, the displacement assembly configured to move the positioning assembly in relation to a surface of the workpiece.

In still another embodiment a method includes providing a sample cutter, supporting at least a portion of an obround blade in the sample cutter, and rotating the obround blade within the base block, external blade guide, and internal blade guide. At least a portion of the sawblade extends beyond the saw end of the base block. The method further includes moving at least the portion of the sawblade extending beyond the saw end of the base block through a sample cutting path including at least a portion of a workpiece.

Various aspects will become apparent to those skilled in the art from the following detailed description and the accompanying drawings.

DETAILED DESCRIPTION OF ILLUSTRATIVE EMBODIMENTS

Aspects of disclosures herein generally concern a sample cutter that provides a band-like continuous blade having an unsupported portion that traverses a semi-circular arc length to remove samples from equipment by passing through a portion of the equipment to remove surface and subsurface samples of sufficient size to perform mechanical tests. The samples can be removed in a non-detrimental manner and with minimal disruption to equipment operation. The traversing blade used in conjunction with the sample cutter is supported using design features of the sample cutter to provide appropriate stiffness to the cutting portion of the blade when first contacting or while sweeping through the sample area. Aspects herein further concern positioning assemblies and displacement assemblies providing controlled degrees of freedom to the sample cutter during installation, cutting, or removal. Additional aspects herein concern methodologies for removing material testing samples from equipment.

The improvements over blades which cannot pass through subsurface can be appreciated through relating earlier sampling techniques to a scoop. Because the scoop can only fit a finite volume of material, and such material cannot pass through the scoop to permit larger-dimension cuts, earlier samples are limited by the size of the scoop, and do not remove samples appropriate for completing all relevant material testing.

The meaning of various terms herein will be apparent from the drawings and their use. However, for avoidance of confusion, an "obround blade" or similar terminology can refer to a blade having a cutting edge or teeth oriented parallel to the axis about which it traverses or rotates. An obround blade is closed to form a continuous loop for rotation. In this regard, an obround blade can include, but is not limited to, blades used with band saws. "Coupling" generally refers to interaction and some capability to work in tandem. Mechanical coupling places two components in contact, either directly or through intervening hardware. Where elements are "removably coupled," they are connected by attachment means which facilitating install or uninstall avoiding destruction or deformation of either component being attached. "Operative coupling" or "communication" (e.g., fluid communication, electrical communication) refers to components working together, even if such components are not in physical contact (though they may be in physical contact). This also alludes to "electrical coupling," where by two components can transmit electricity or signals between one another.

Figure 1A:
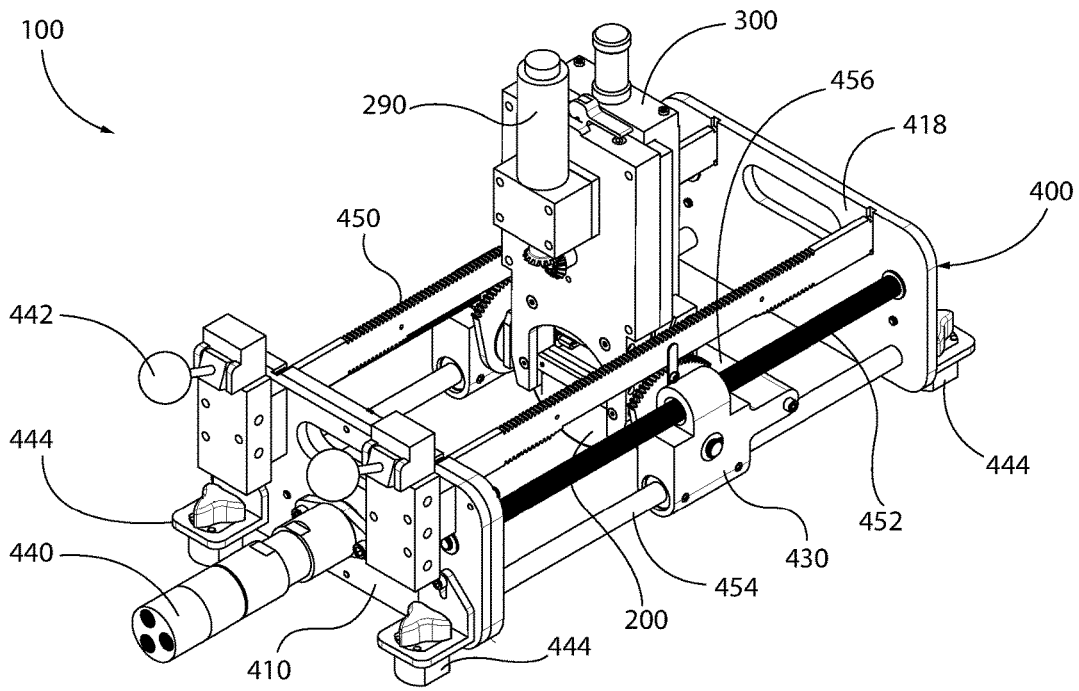
FIGS. 1A and 1B illustrate views of an example sample cutting apparatus.
Figure 1B:
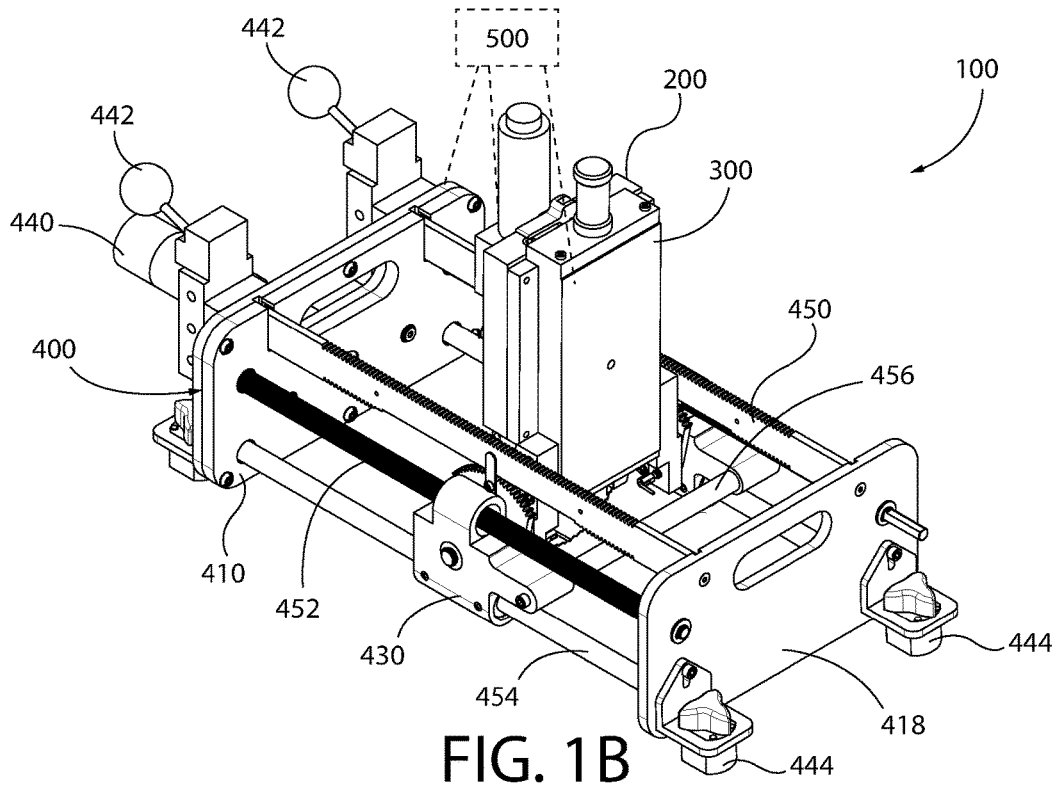

FIGS. 1A and 1B illustrate views of a sample cutter apparatus 100. Sample cutter apparatus 100 generally includes a cutting assembly 200, positioning assembly 300, and displacement assembly 400. According to an example, cutting assembly 200 pivots on positioning assembly 300 to engage the material from which a sample is taken, the cutting assembly 200 may then be moved by displacement assembly 400 while engaged with the material to elongate the cutting area within the material and then pivoted again by the positioning assembly 300 to terminate the cut and exit the material. FIGS. 1A and 1B provide non-limiting context for the sample cutter apparatus 100 described hereafter in terms of its movement and employment, and will be discussed in further detail below.

Cutting assembly 200 includes a blade 210 or other cutting element having an unsupported section to cut a material sample suitable for testing. In the examples shown, obround blade 210 may include an elongate blade, which may be flexible, such as a band saw blade. It will be understood, that other cutting elements may be employed in cutting assembly 200 as well. With reference to the examples shown in the accompanying figures, a flexible band saw blade is used as an obround blade 210. The blade is rotationally driven to perform its cutting operation. Rotational force from a motor may be delivered to the blade in a number of manners including drive wheel with pressure plate as shown. To ensure that the blade substantially maintains a desired arc or other contour for cutting the sample, appropriate guides are provided to maintain stiffness of the blade and/or assist the blade in maintaining the desired shape as will be described in more detail below.

Figure 2A:
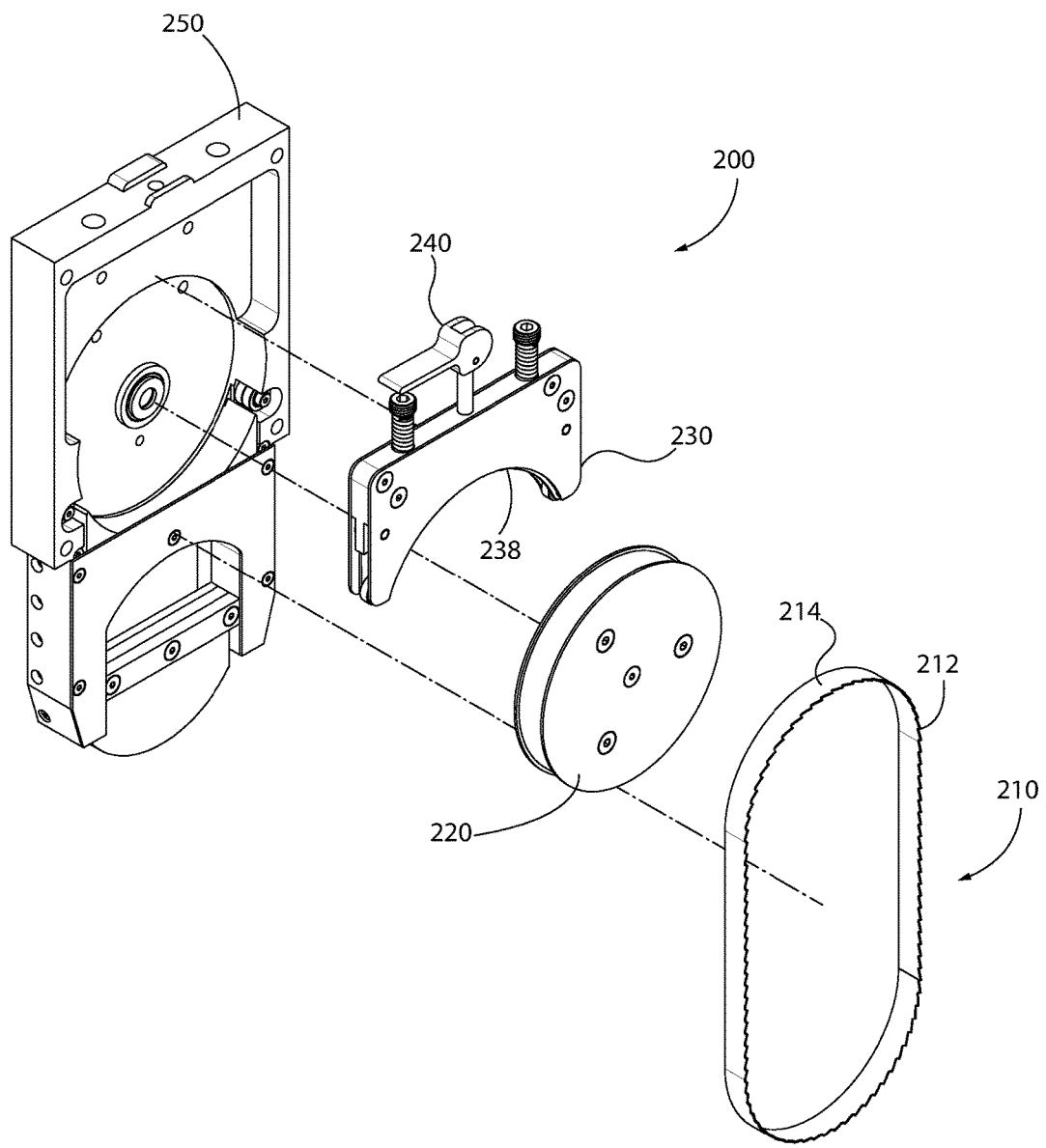
FIG. 2A illustrates an exploded view of an example sample cutter.
Figure 2B:
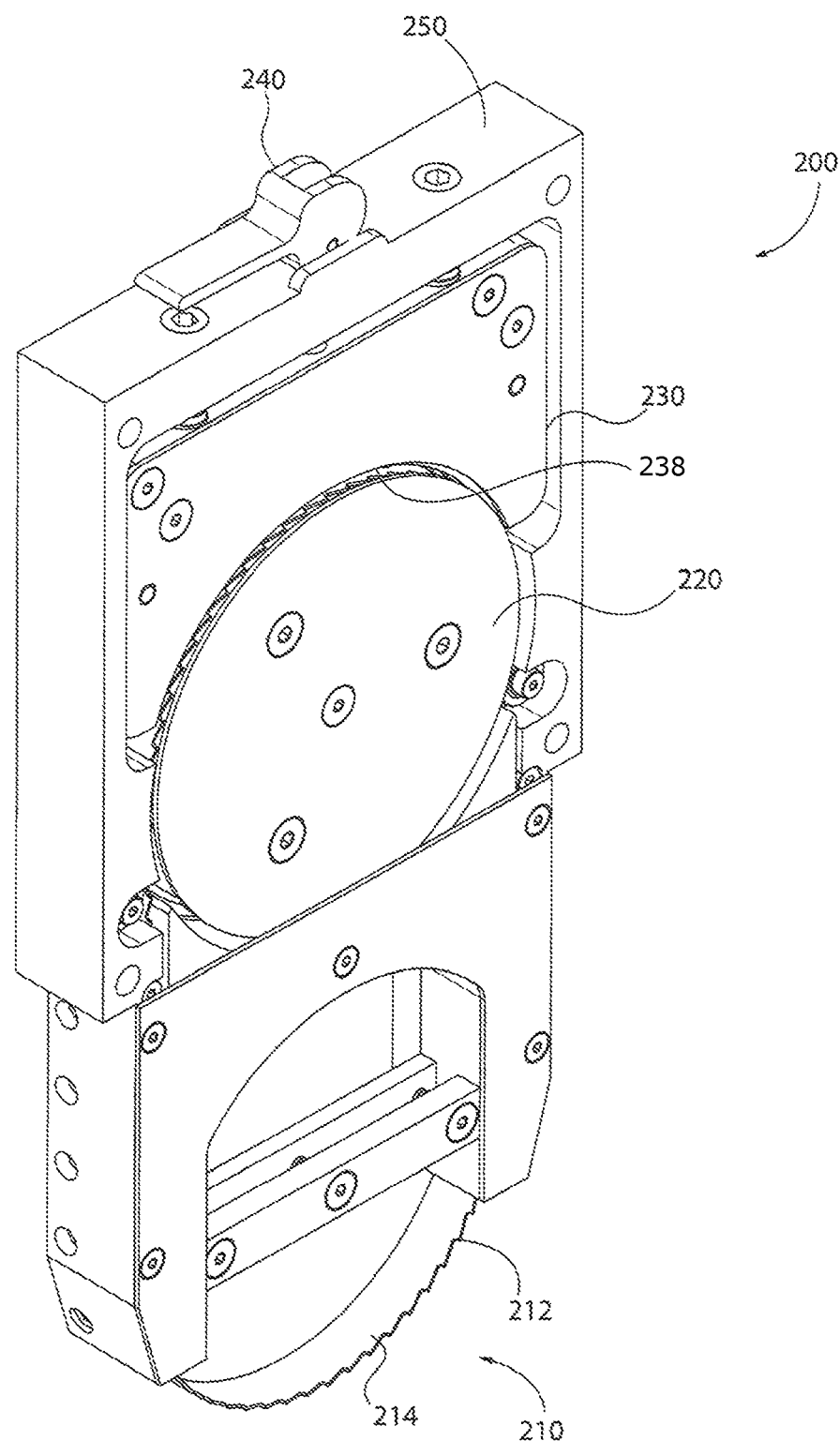
FIG. 2B illustrates a composite view of an example sample cutter.
Figure 3:
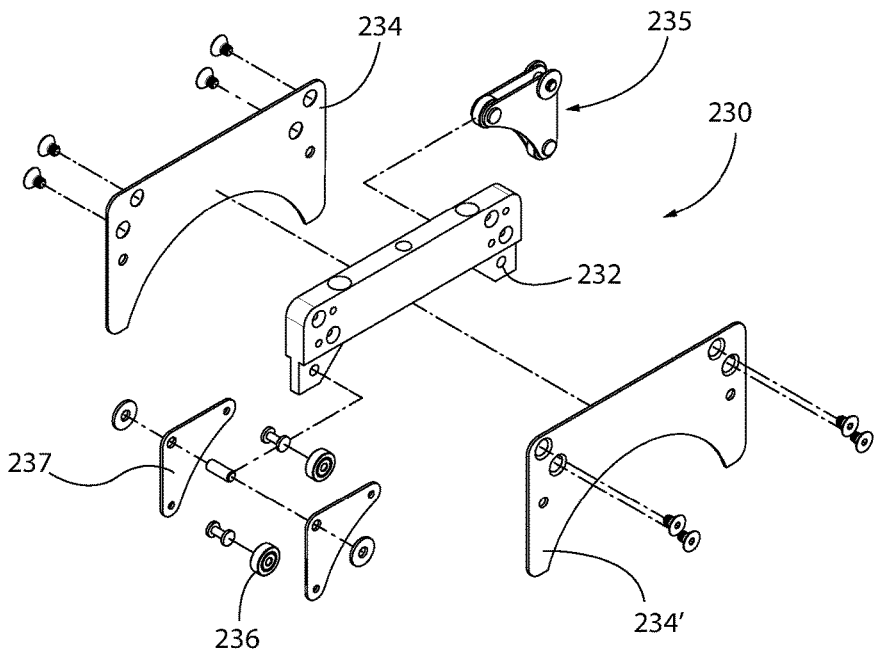
FIG. 3 illustrates an exploded view of an example saw pressure plate for use with a sample cutter.
Figure 4:
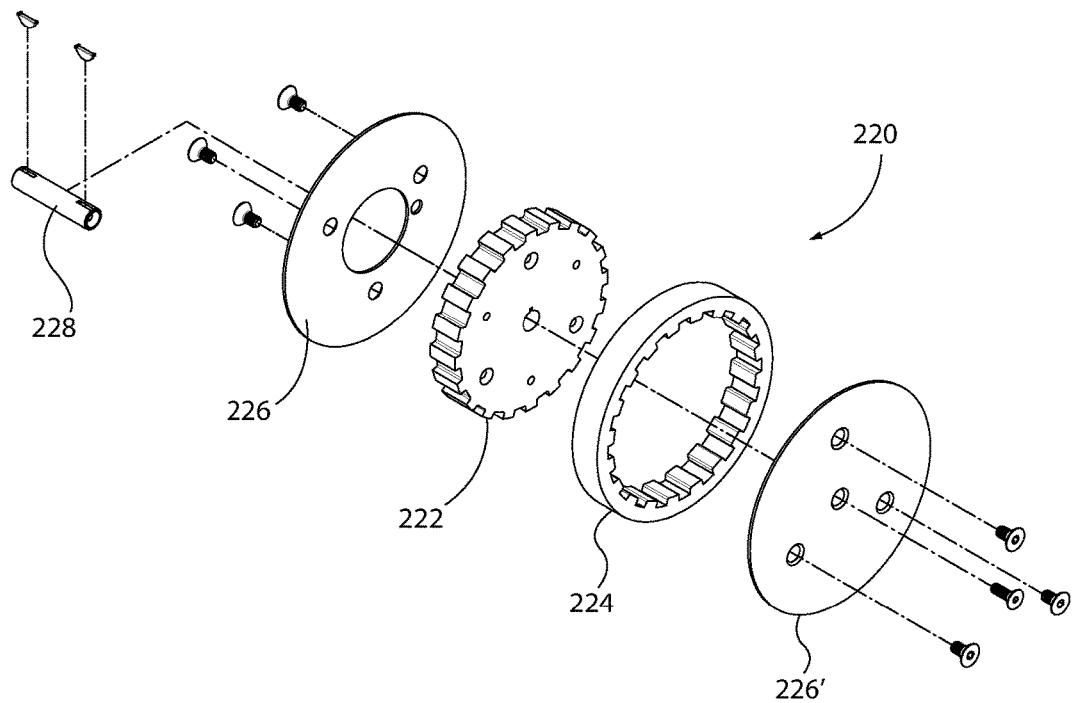
FIG. 4 illustrates an exploded view of an example saw drive wheel for use with a sample cutter.
Figure 5:
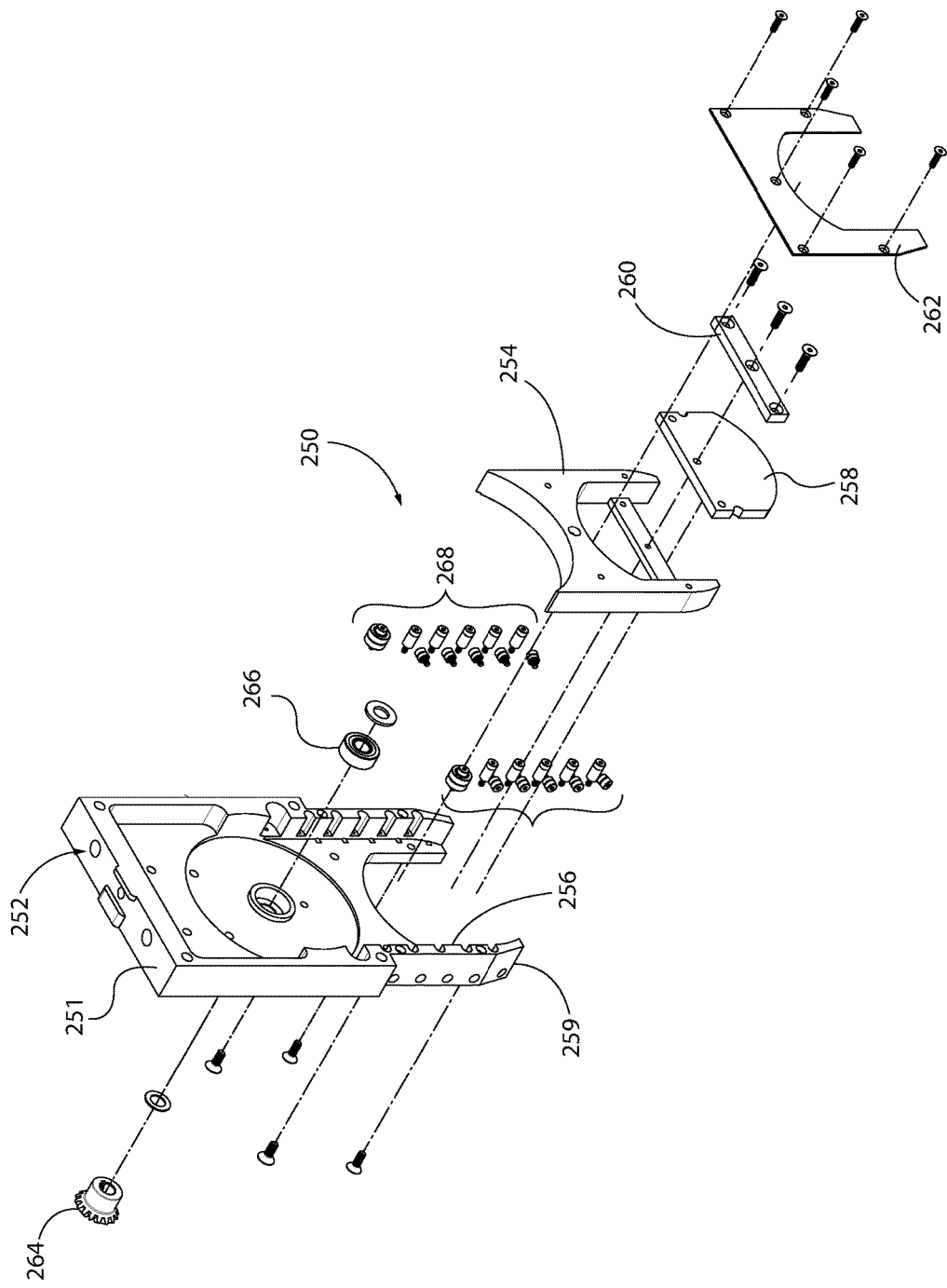
FIG. 5 illustrates an alternative exploded view of an example sample cutter.
Figure 6A:
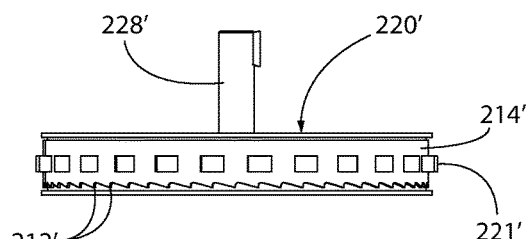
FIGS. 6A, 6B, 6C, and 6D illustrate views of an alternative example drive mechanism for a sample cutter.
Figure 6B:
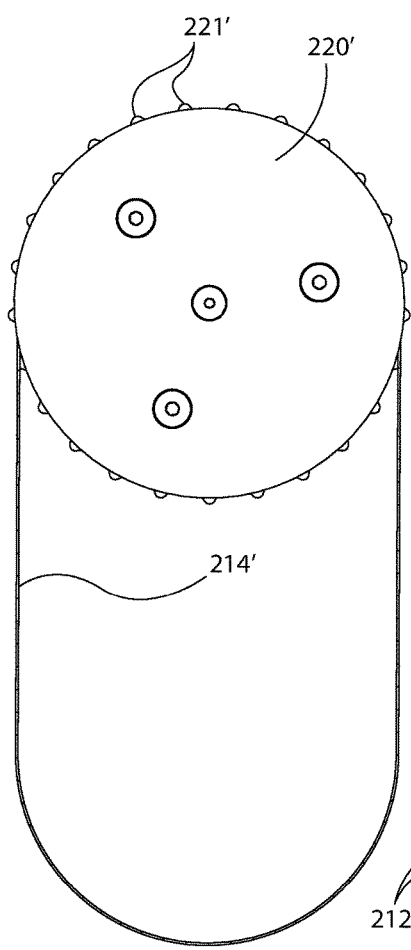
Figure 6C:
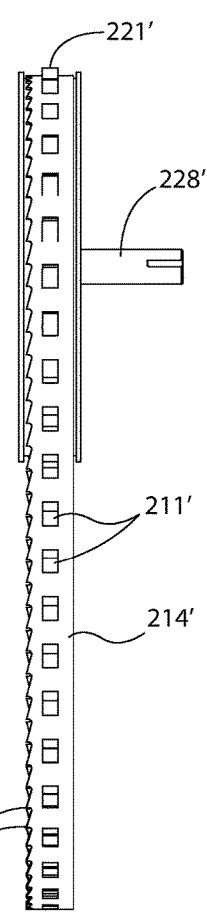
Figure 6D:
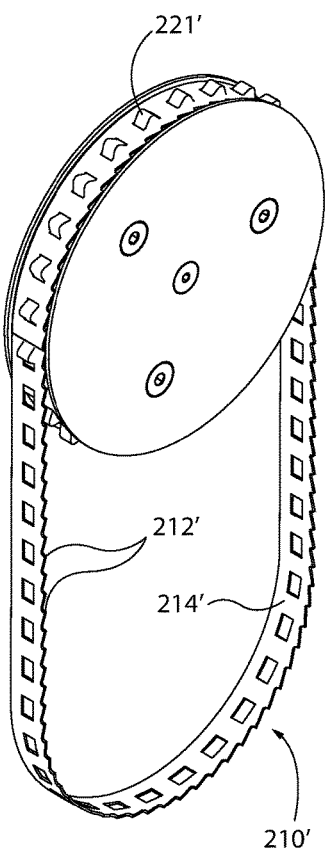
Figure 7:
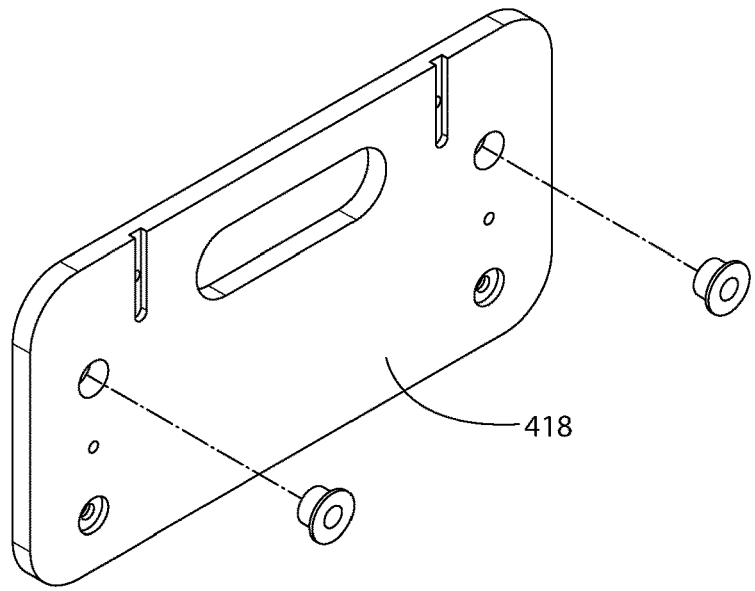
FIG. 7 illustrates an example endplate for a displacement assembly used in conjunction with a sample cutter.
Figure 8:
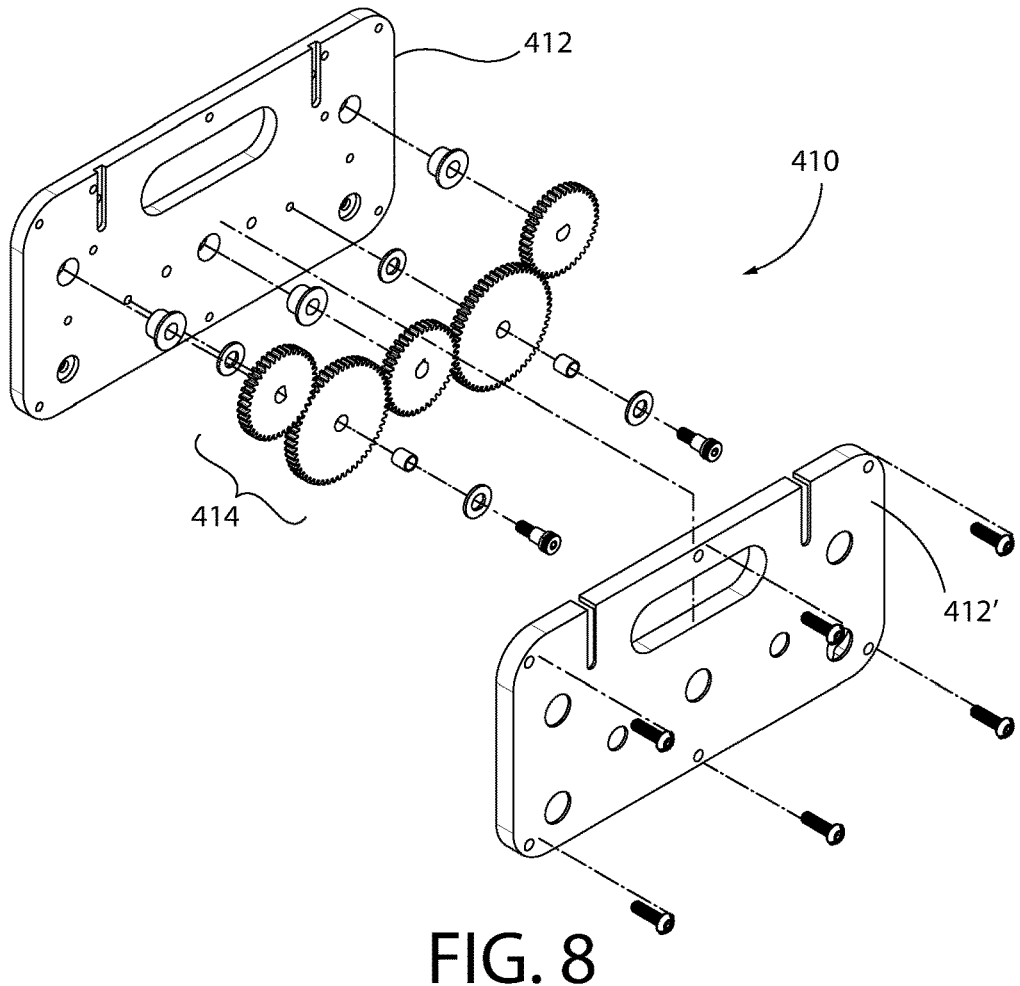
FIG. 8 illustrates an exploded view of an example gearbox for a displacement assembly used in conjunction with a sample cutter.
Figure 9:
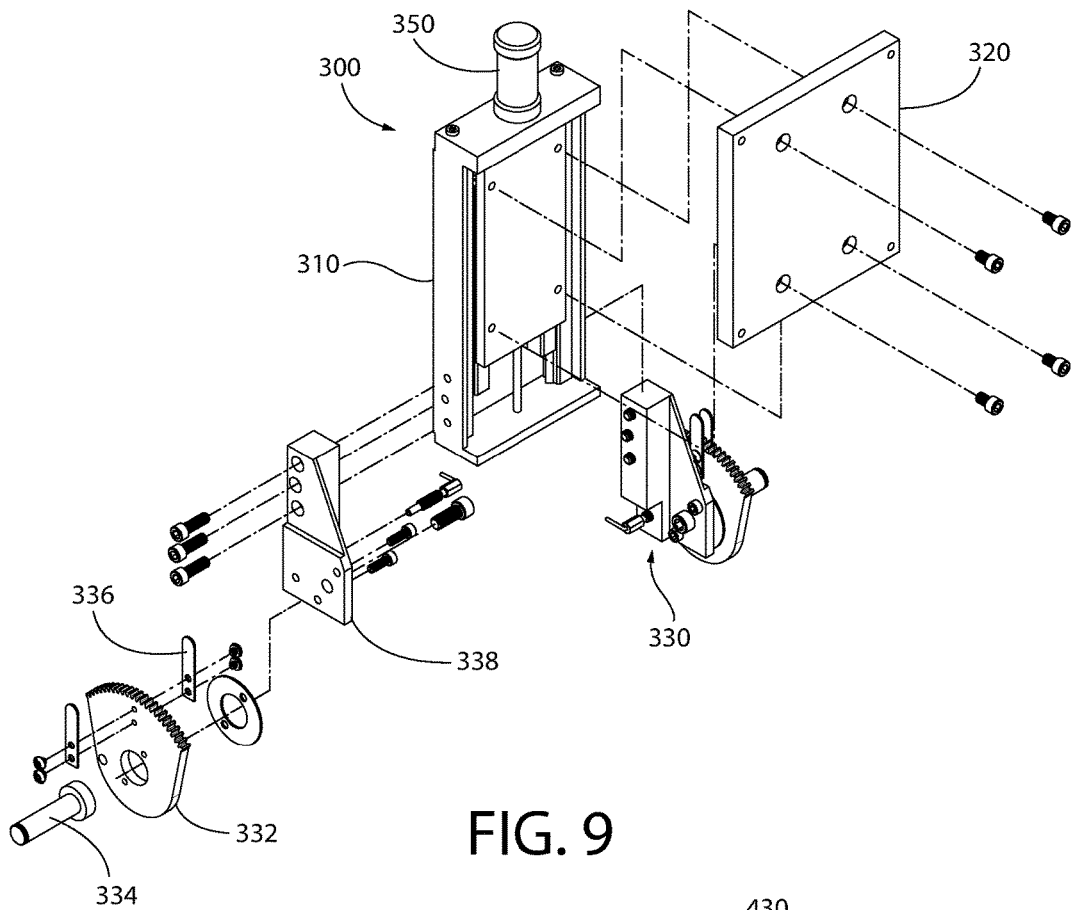
FIG. 9 illustrates an exploded view of an example positioning assembly for use with a sample cutter.
Figure 10:
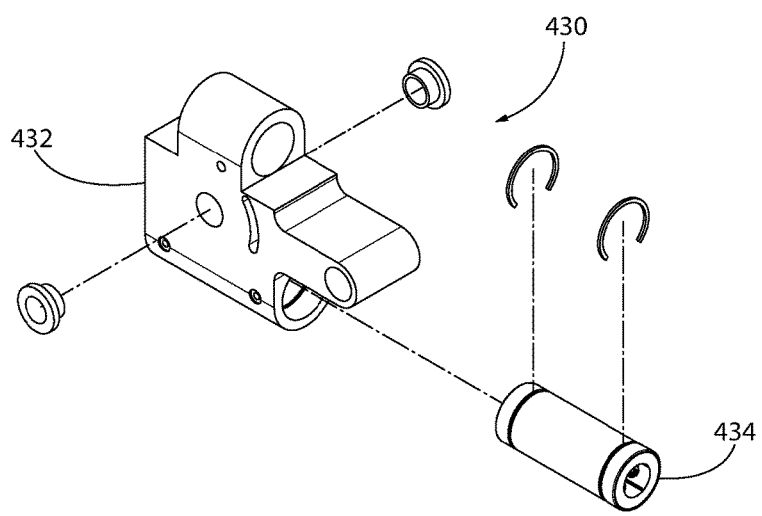
FIG. 10 illustrates an exploded view of an example travel guide for use with a displacement assembly and sample cutter.

FIG. 2A illustrates an exploded view of cutting assembly 200, and FIG. 2B illustrates a fully assembled cutting assembly exhibiting an unsupported semi-circular portion of the obround blade 210. FIG. 3 illustrates an exploded view of saw pressure plate 230 for use with cutting assembly 200 and FIG. 4 illustrates an exploded view of a drive wheel 220 for use with sample cutting assembly 200. FIG. 5 illustrates an alternative exploded view of sample cutting assembly 200 with internal blade guide 254 removed.

Cutting assembly 200 may include a sample cutter base 250, saw pressure plate 230, saw drive wheel 220, and internal blade guide 254. Sample cutter base 250 includes base block 252 having drive end 251 and saw end 259. Drive end 251 is the portion of base block 252 distal to the workpiece when sample cutting assembly 200 is in operation. Saw end 259 is the portion of base block 252 from which a saw blade can extend when installed. Base block 252 includes saw pressure plate 230 disposed within base block 252 toward drive end 251. Toward saw end 259, base block 252 defines external blade guide 256, and disposed at least partially therebetween is removable internal blade guide 254. Saw pressure plate 230, external blade guide 256, and internal blade guide 254 define the contours through which a saw blade can be installed and move, and support or constrain such saw blade to ensure sufficient stiffness in unconstrained portions (e.g., cutting portion of the saw when in operation) to prevent deflection, deformation, or other loss of cutting effectiveness.

In the embodiment illustrated, saw pressure plate 230 can include pressure plate hub 232, pressure plate caps 234 and 234', swivel plate(s) 237, and bearing(s) 236 (and similar components varied based on opposing geometry). In such embodiments pressure plate hub 232 and pressure plate caps 234 and 234'; swivel plate(s) 237, and bearing(s) 236 define pressure surface 238 from which contact pressure is distributed to a portion of the blade in an effort to generate the required frictional force between the blade and drive wheel tire to propel the blade during sample removal. In further embodiments such as that illustrated, saw pressure plate can include one or more pressure bearing(s) 236 which facilitate unobstructed rotation of an installed saw blade. In alternative embodiments more or fewer pressure bearings can be included in saw pressure plate 230, to include none at all. In further alternative or complementary embodiments, saw pressure plate may be coupled with saw blade release 240 which can be toggled to secure or unsecure an installed saw blade for installation or removal. Additionally, saw pressure plate 230 guides and externally supports an installed saw blade to prevent it from displacing or buckling when loads are applied during cutting at saw end 259. At swivel plate(s) 237 and bearing(s) 236, with other hardware, can be combined to form swivel plate assemblies 235. Swivel plate assemblies 235 can utilize spring forces to transfer the load applied to the pressure plate to the saw blade. Their swiveling action assures self-alignment and can in embodiments assist with distribution of applied forces.

In specific embodiments such as that illustrated, internal blade guide 254 can be coupled with additional components such as movable blade guide 258. Movable blade guide 258 is attached to internal blade guide 254 using movable blade guide plate 260. Movable blade guide 258 can be a flexible element comprised of one or more of, e.g., foam, rubber, plastic, spring metals, or other appropriate materials which will deflect opposite the cutting direction during operation. Movable blade guide 258 provides support against inward or lateral collapse (e.g., folding or deflection into internal blade guide 254 when radial or tangential force components are applied from the external circumference of the blade toward the internal circumference, such as when an installed blade initially contacts a workpiece for cutting or reaction forces on the blade during cutting). Movable blade guide 258 can also limit vibration in the unsupported portion of a blade. However, once the blade begins cutting, movable blade guide 258 bends or deflects opposite the direction of cut to permit the sample being cut to pass through the inner portion of the unsupported blade without disruption or significant resistance. Collapse of the blade during this time is unlikely as the channel being cut and partially-cut material serve to prevent unwanted flexion of the blade. After cutting is complete and sample material removed from inside of the obround cutting blade, movable blade guide 258 restores itself to its original position as illustrated.

Internal guide cap 262 can also be placed over at least a portion of internal blade guide 254 and external blade guide 256 in embodiments, providing another constraint against deflection or inadvertent removal of an installed saw blade by preventing the blade's movement in a direction orthogonal to support provided by external blade guide 256 and internal blade guide 254. External blade guide 256 (and, in embodiments alternative or complementary to that depicted) can also retain one or more blade bearings 268 for encouraging smooth travel of an installed obround blade.

In embodiments such as that depicted, saw drive wheel 220 is disposed within base block 252 between saw pressure plate 230 and internal blade guide 254. As illustrated, saw drive wheel 220 can include drive wheel 222, drive wheel tire 224, drive wheel caps 226 and 226', and drive shaft 228. Drive shaft 228 can couple with drive gearing 264 and/or drive bearing 266. Drive gearing 264 is configured to communicate mechanically with a saw drive motor. In alternative embodiments, other techniques may be utilized for employing a saw constrained by internal and external guides and/or a pressure plate.

In further embodiments, the use of external blade guide 256 and internal blade guide 254 in combination with saw drive wheel 220 and saw pressure plate 230 can ensure stiffness is maintained on the blade to further resist buckling or excessive distortion.

In further embodiments, sample cutter base 250 include a drive mounting portion configured to mount a saw drive motor in a manner facilitating actuation of an installed saw blade.

Obround saw blade 210 appropriate for use with a sample cutting assembly 200 is shown in, e.g., FIG. 2. Obround saw blade 210 can have a circumference (or length), a width (e.g., the larger axial dimension parallel to the axis or axes about which the blade rotates), and a thickness (e.g., the width of the cutting edge or rear non-cutting edge). Obround saw blade 210 can be a round saw blade or other appropriate blade which cuts through rotation about an axis or axes parallel to the width of the blade, e.g., the axial direction. As illustrated, obround saw blade 210 includes at least teeth 212 and band 214. In at least one embodiment, teeth 212 can be realized using, or replaced or supplemented by a grit (e.g., carbide grit, diamond grit) or other cutting surface.

In embodiments, obround saw blade 210 is disposed partially within base block 252, and in at least partial contact with saw pressure plate 230 near drive end 251 of the base block. Further, at least a portion of an external circumference of obround saw blade 210 is contained within external blade guide 256, and at least a portion of an internal circumference of obround saw blade 210 is disposed around internal blade guide 254, with a cutting portion of obround saw blade 210 extending beyond saw end 259 of the base block. Obround saw blade 210 can be any appropriate blade of any appropriate material, and is sized or configured to extend beyond saw end 259 such that samples of the desired size can be cut when obround saw blade 210 is in contact or adjacent to the above-described elements. Obround saw blade 210 is exchangeable and replaceable with new or different saw blades of sufficient length for installation.

Obround saw blade 210 (and any other blades in alternative embodiments) abide particular material and geometric parameters to prevent buckling of the blade during operation. Such parameters include bend radius, the length of the unsupported arc of blade, blade thickness, blade width, blade elastic modulus, blade material hardness, et cetera. Such parameters are interdependent, and adjusting one parameter may require adjustment to other parameters if buckling or other deformation is to be avoided under a given load.

Turning to FIGS. 6A to 6D, an alternative drive mechanism 220' for use with alternative blade 210' is illustrated. Drive mechanism 220' includes drive shaft 228' and employs cogs 221' matched to blade apertures 211' of obround blade 210' to ensure non-slipping movement of obround blade 210'. Obround blade 210' also includes teeth 212' and band 214'. While FIGS. 6A to 6D show an alternative embodiment to the tire embodiment depicted elsewhere herein, those of skill in the art will appreciate still other techniques for driving an obround saw blade, and these disclosures are intended to convey concepts for saw drive rather than exhaustive or exclusive listings of embodiments.

Regardless of which drive mechanism is employed—220, 220', or alternatives—a motor such as saw drive motor 290 can be coupled with sample cutting assembly 200 to provide power to the drive mechanism. In alternative or complementary embodiments other arrangements can be developed through gears, linkages, et cetera, to permit other power sources (e.g., various motors or positioning elements herein) to move an obround saw blade installed to sample cutting assembly 200.

Turning to techniques for employing the sample cutter, FIGS. 1A, 1B, and 7 to 10 illustrate other components of sample cutter apparatus 100 used therewith. While sample cutting assembly 200 can be coupled to or used with these elements, its discussion herein is limited in view of the details provided above. Nonetheless, all aspects set forth above and others appreciated through discussion hereafter apply equally throughout this specification.

Sample cutter apparatus 100 can include sample cutting assembly 200 for use with positioning assembly 300 and displacement assembly 400. Positioning assembly 300 can be coupled with the sample cutting assembly 200, and is used to raise, lower, or rotate sample cutting assembly 200 with respect to a workpiece. In this regard, positioning assembly 300 is configured to move sample cutting assembly 200 toward or away from the workpiece, and may rotate sample cutting assembly 200 to permit the blade to encounter the workpiece at an angle appropriate for cutting then guide the blade through the sample path.

As illustrated, positioning assembly 300 includes slide assembly 310 for moving sample cutting assembly 200 toward or away from the workpiece. This and other elements of positioning assembly 300 can be positioned by, e.g., positioning element 350 or other components. Positioning assembly 300 can also include at least one spindle assembly 330 mechanically coupled to positioning assembly 300. Spindle assembly 330 is configured to rotate the positioning assembly 300 in relation to a surface of a workpiece, and can include spindle gear 332, spindle 334, pivot stop 336 (e.g., to aid in spindle gear 332 to displacement rack 450 gear tooth alignment), and spindle plate 338. Alternative or complementary rotation components can be used independently or in combination with spindle assembly 330.

Positioning element 350 can be a precision lead screw or other positioner, and may be manually operated or automated. In embodiments, positioning element 350 can be a positioning drive motor. While positioning element 350 and other drive mechanisms herein may be described as motored, manually-operated, or moved according to various other techniques, it is understood in view of this disclosure that such aspects may be interchangeable without departing from the scope or spirit of the innovation.

Displacement assembly 400 is mechanically coupled with at least positioning assembly 300. Displacement assembly 400 is configured to move positioning assembly 300 in relation to a surface of a workpiece. Displacement assembly can be defined by fixed components at the ends of its length, which can include endplate 418 and gearbox 410. Gearbox 410 can further include gearings 414 and gearbox caps 412 and 412'. Displacement drive motor 440 and air valves 442 can be coupled to at least gearbox 410. In an embodiment, air valves 442 can be used to receive compressed air for air drive functions complementary or alternative to displacement drive motor 440. Further coupled to one or both of gearbox 410 and endplate 418, attachment assembly 444 is configured to removably couple the sample cutting apparatus with a workpiece. In embodiments, attachment assembly 444 includes magnetic elements. In alternative or complementary embodiments, suction cup devices can be used (e.g., with non-ferromagnetic materials). In still further complementary or alternative embodiments, attachment assembly 444 can include a magnetic creeper (or other translatable attachment sub-assembly) to move the cutter's positioning in relation to the workpiece remotely.

Displacement assembly 400 can further include travel guide 430 comprising travel guide block 432 and linear bearing 434 to assist with displacement or stabilizing of sample cutting assembly 200 and/or positioning assembly 300. Displacement assembly 400 can further include displacement rack 450, threaded displacement rod 452, hardened shaft 454, cross brace 456, and/or other elements for traversing various components about a workpiece. Generally speaking, the dimensions of displacement rack 450, threaded displacement rod 452, and hardened shaft 454 define a maximum sample length, and so can be designed or adjusted to achieve various sample lengths.

While displacement assembly 400 shows the ability to translate its coupled components along a linear path, alternative or complementary embodiments can include a displacement assembly capable of moving other assemblies in additional directions. In this manner, multiple samples may be taken from a single installation, and more accurate sample locations can be cut without repositioning the entire apparatus. Further, if coupled with the capability to rotate the saw about the axis orthogonal to the workpiece surface (e.g., another degree of rotational freedom for positioning assembly 300), samples can also be cut in various directions without repositioning displacement assembly 400 and coupled structures.

Sample cutter apparatus 100 can also include a controller 500 in one or more of the assemblies (e.g., sample cutting assembly 200, positioning assembly 300, displacement assembly 400) or at a remote location where the assemblies include wired or wireless ports for receiving signals. Controller 500 can at least control operation of the motors to displace, position, and/or rotate the assemblies, and/or cause obround blade 210 to spin or cease spinning to enable cutting. Controller 500 may be automated, manual, or a combination thereof, and may also send and receive data related to at least operation of sample cutter apparatus 100. In an embodiment, sensed resistance to cutting can be used to indicate a mismatch between blade type and material, or excess wear in a blade. Warnings and alarms can be provided wear motors, connected drive shafts, or other components stall, slip, fail, et cetera. In alternative or complementary embodiments, unexpected ease of cutting can be used to discern over-cuts which cut entirely through a workpiece rather than removing a sub-surface sample that does not compromise the workpiece's structural integrity. Controller 500 can permit reversal of an undesired cut to avoid full removal of the sample and ease repairs. Other logic can be employed for various alternative control and data gathering functions.

Figure 11A:
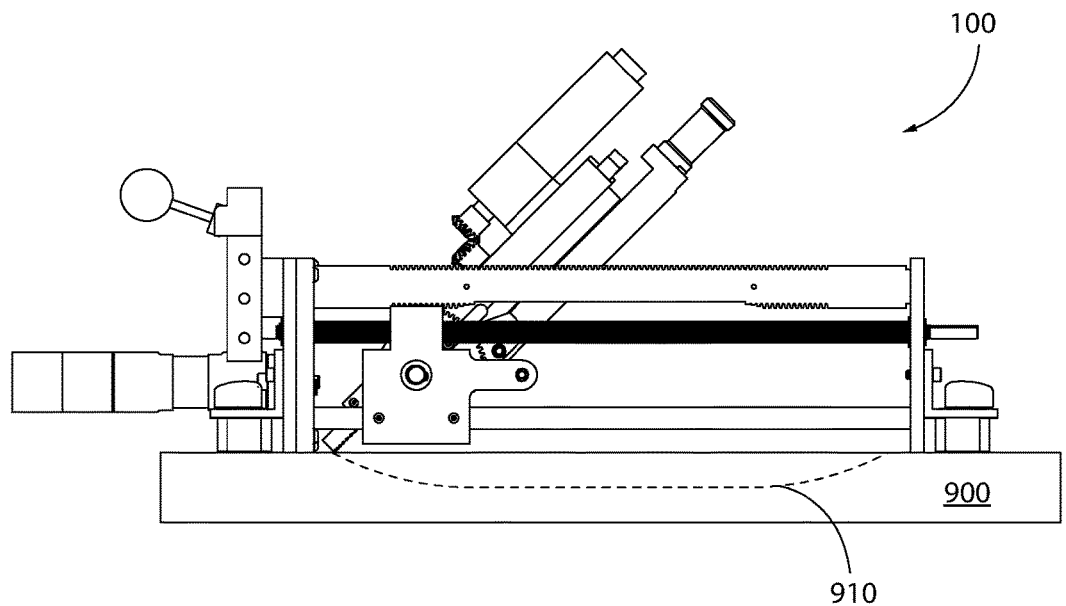
FIGS. 11A, 11B, 11C, and 11D illustrate views of an example sample cutting apparatus cutting through a cutting path on a workpiece.

FIGS. 11A to 11D illustrate an example process using a sample cutting apparatus as disclosed herein. FIG. 11A shows sample cutter apparatus 100 attached to workpiece 900 and arranged to cut a sample defined by cutting path 910.

Figure 11B:
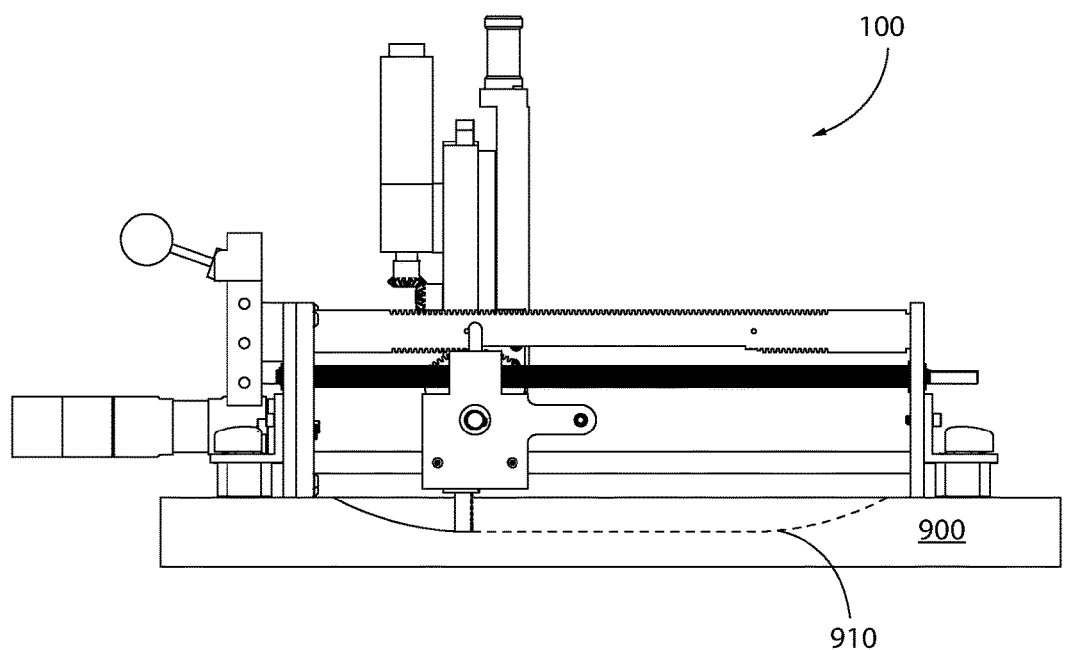

As the obround blade cuts into the surface of workpiece 900, the positioning assembly and sample cutting assembly are rotated and level after reaching the cut depth, shown in FIG. 11B. In this regard, the obround blade (e.g., 210) has a maximum depth defined by the vertical distance (measured in a direction e.g., parallel to the plane defined by the face of internal guide cap 262) between the blade's bottom-most edges (e.g., extending beyond saw end 259) and the bottom-most edges of the sample cutting assembly (e.g., 200, and more particularly external blade guide 256, internal blade guide 254, and internal guide cap 262, the bottom-most portions of the assembly). The saw is arranged such that the cut depth facilitates clearance or at least friction still permitting movement between the workpiece and non-cutting portions of the sample cutting assembly. Saw blades (and, in some embodiments, movable blade guides) can be configured and provided to facilitate different cut depths. In embodiments, appropriate saw blade length can be determined as a function of saw blade material or stiffness to ensure the blade does not collapse, bend, or otherwise compromise the cut or apparatus during operation.

Figure 11C:
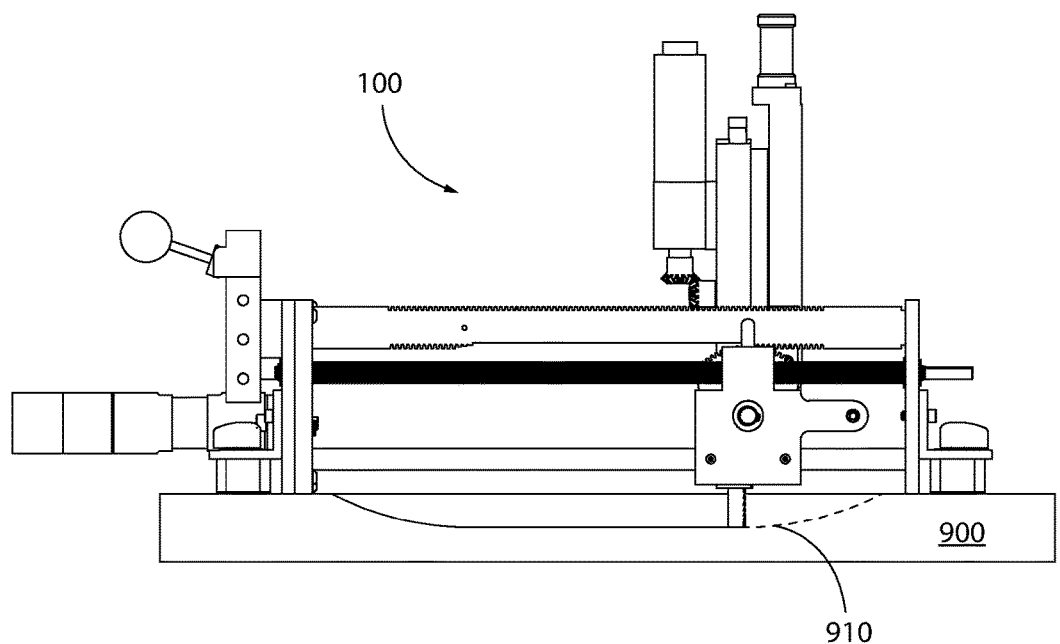
Figure 11D:
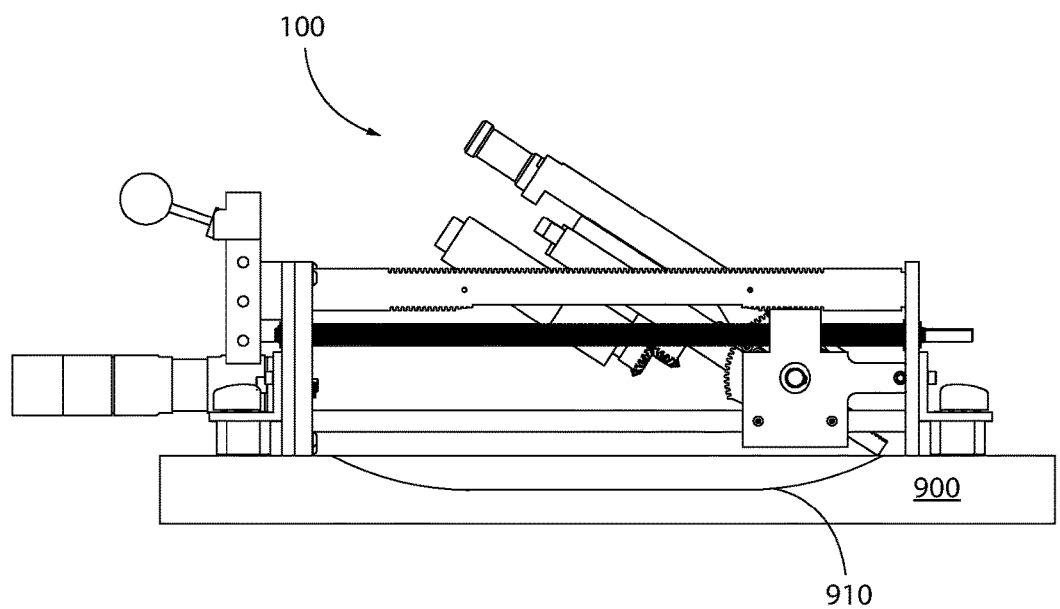

FIG. 11C shows the blade at the cutting depth, now rotated to cut substantially parallel to the face of the workpiece, traveling through the cut length for the desired sample size. In FIG. 11D, the positioning assembly rotates the sample cutter out of the workpiece to free the sample and sample cutting apparatus. The sample can then be removed and sample cutting apparatus detached and removed or installed at another location for additional sample cutting.

In an alternative embodiment, the rotating obround blade can be used to cut only a portion of a sample having a uniform cross-section, with tapering edges of a sample (e.g., where the sample height varies or tapers along the sample length) cut by another mechanism. In such embodiments, an alternative cutter (excluding, in comparison to embodiments shown above, e.g., a pressure plate or portions thereof, a movable blade guide, some or all of an internal or external blade guide, spindles or other rotating mechanisms) may be employed. For embodiments in which the rotating blade only sweeps through portions of uniform cross-section, loads on the blade will not be borne in or from directions, or in magnitudes, as would be encountered during the blade's initial bite into the workpiece and during rotation through the tapered ends of the workpiece before proceeding through the substantially linear cutting path. In this regard, scoop or other angled or rotating cutters can be used to begin the cut into the workpiece for sample extraction and the rotating obround blade can be arranged within an existing cut for its use in the process.

Figure 12A:
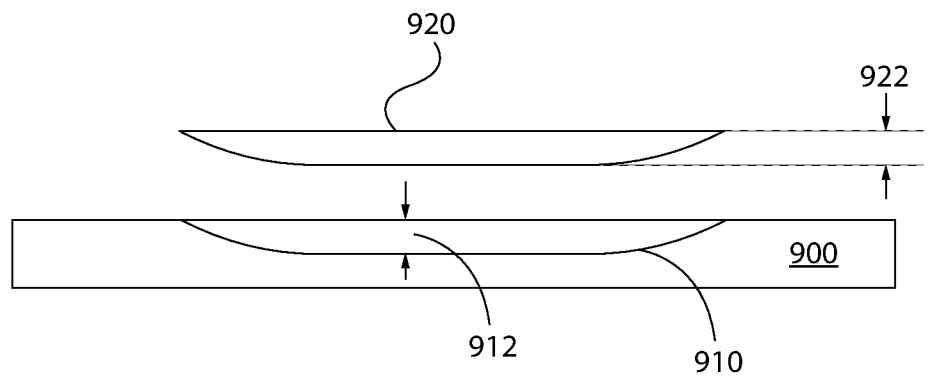
FIGS. 12A and 12B illustrate views of example samples and sample areas in a workpiece.
Figure 12B:
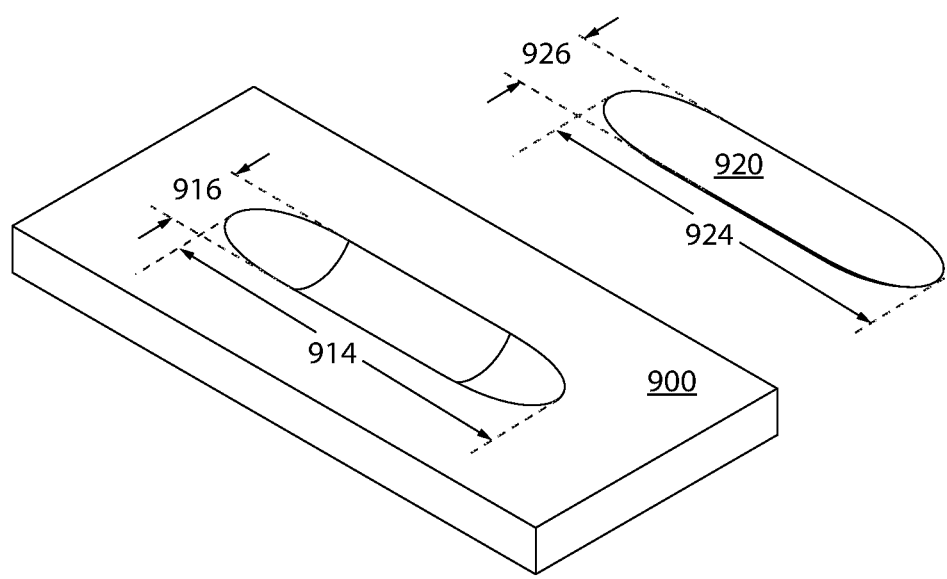

FIGS. 12A and 12B illustrate various views of a sample 920 cut from workpiece 900. Sample 920 has a sample height 922, a sample length 924, and a sample width 926, respectively corresponding to a cut depth 912, cut length 914, and cut width 916. These dimensions, dependent on saw blade length, can be cut large enough to permit any type of material testing to determine the serviceability or condition of workpiece 900. While workpiece 900 is shown as a linear block for ease of explanation, it is understood that workpiece 900 may be a curved pressure vessel wall, asymmetrical or non-planar piece, et cetera.

A method reflecting the techniques illustrated in, e.g., FIGS. 11A to 11D can include providing a sample cutter including a base block configured to couple with a positioning assembly, the base block having a saw end and a drive end, a saw pressure plate disposed within the base block toward the drive end of the base block, an external blade guide disposed toward the saw end of the base block, and an internal blade guide disposed toward the saw end of the base block and at least partially within the external blade guide. Thereafter the method can include supporting at least a portion of a circumference of an obround blade in the sample cutter, then rotating the obround blade within the base block, external blade guide, and internal blade guide, at least a portion of the sawblade extends beyond the saw end of the base block. The method can further include moving at least the portion of the sawblade extending beyond the saw end of the base block through a sample cutting path including at least a portion of a workpiece.

In various embodiments methods can further include providing a displacement assembly configured to move the sample cutting assembly in relation to a surface of the workpiece. In alternative or complementary embodiments, methods can further include attaching the displacement assembly to the workpiece. In additional embodiments, methods can include providing a positioning assembly mechanically coupled with the sample cutter, the positioning assembly configured to move the sample cutter toward or away from a workpiece. In still further embodiments, methods can include rotating the base block in relation to a surface of the workpiece.

In the specification and claims, reference is made to a number of terms described hereafter. The singular forms "a," "an," and "the" include plural referents unless the context clearly dictates otherwise. Approximating language, as used herein throughout the specification and claims, may be applied to modify a quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Moreover, unless specifically stated otherwise, a use of the terms "first," "second," etc., do not denote an order or importance, but rather the terms "first," "second," etc., are used to distinguish one element from another.

As used herein, the terms "may," "may be," "can," and/or "can be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As utilized herein, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A, or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

To the extent that the term "includes" is used in either the detailed description or the claims, such term is intended to be inclusive in a manner similar to the term "comprising" as "comprising" is interpreted when employed as a transitional word in a claim.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A sample cutter comprising:
a continuous blade having a first end having a cutting edge and a second end having a cutting edge;
a base block enclosing the first end of the blade, the base block defining a blade channel receiving the first end of the blade therein, wherein the blade channel includes a pair of blade openings that open at a saw end of the base block such that a cutting portion of the second end of the blade extends beyond the base block traversing a cutting arc, the entire second end of the blade being unsupported by the base block during a cutting operation; wherein the base block includes an internal guide surface and an external guide surface forming a portion of the blade channel within the saw end of the base block adjacent to the blade openings, wherein at least one of the internal guide surface and the external guide surface apply a pre-stress to the continuous blade to maintain the cutting arc during the cutting operation;
a drive assembly supported on the base block, the drive assembly engaging the blade to move the blade along the cutting arc during the cutting operation, wherein the drive assembly includes a drive wheel;
a pressure device defining a portion of the blade channel, the pressure device engaging a second surface of the continuous blade applying a pressure to the first end of the blade toward the drive wheel; and
a moveable blade guide displaceable between a first position where the blade guide lies within the cutting arc to engage an inner surface of the continuous blade and a second position where the moveable blade guide disengages the inner surface of the continuous blade;

the moveable blade guide being displaceable in a direction opposite the cutting direction, the movable blade guide having an arcuate guide surface that matches the inner surface of the cutting arc.

2. The sample cutter of claim 1, wherein the drive wheel includes plural cogs.

3. The sample cutter of claim 1 further comprising a travel guide supported on a slide assembly defining an axis, the travel guide being configured to translate along the axis of the slide assembly; wherein the base block is pivotally attached to the travel guide by a spindle assembly, the spindle assembly defining an arc through which the base block is rotated including a position where the blade block is perpendicular to the axis.

4. The sample cutter of claim 1, wherein the internal guide surface is spaced from the external guide surface to define a pair of side portions of the blade channel, the side portions of the blade channel extending parallel to each other inward from the blade openings toward the drive wheel.

5. The sample cutter of claim 1 wherein the internal guide surface and external guide surface are spaced relative to each other to define substantially parallel side sections of the blade channel, and wherein the continuous blade is sized such that an initial force is applied to the continuous blade to insert the continuous blade in side sections to induce the pre-stress.

6. The sample cutter of claim 1, wherein the pressure device includes a pressure plate hub, one or more pressure plate caps mechanically coupled to the pressure plate hub, and one or more swivel bearings engageable with the second surface of the blade.

7. The sample cutter of claim 1, wherein the moveable blade guide comprises a flexible member.

8. The sample cutter of claim 1, wherein the moveable blade guide is biased toward a position perpendicular to the interior surface of the blade.

9. The sample cutter of claim 1, wherein the internal guide surface is removably attached to the base block.

10. The sample cutter of claim 1, wherein the external guide surface includes at least one roller engaging the second surface of the blade.

11. The sample cutter of claim 1 further comprising an attachment assembly configured to removably couple the sample cutter to a work piece.

12. The sample cutter of claim 1, wherein the pressure device includes a pressure surface that is curved to conform to a portion of the drive wheel.

13. The sample cutter of claim 1, wherein the continuous blade is an obround blade.

14. A sample cutter comprising:
a continuous blade having a cutting edge;
a base block enclosing a portion of the blade, the base block defining a blade channel receiving the first end of the blade therein, wherein the blade channel includes a pair of blade openings that open at a saw end of the base block such that a cutting portion of the second end of the blade extends beyond the base block traversing a cutting arc; wherein the base block includes an internal guide surface and an external guide surface forming a portion of the blade channel within the saw end of the base block adjacent to the blade openings;
a travel guide pivotally supporting the base block, wherein the continuous blade rotates about an axis of rotation defined by the travel guide between a first position where the cutting edge enters a workpiece and a second position where the cutting edge exits the workpiece, wherein the travel guide further defines an intermediate position where the cutting edge lies parallel to an outer surface of the workpiece;
a displacement assembly, the displacement assembly configured to translate the blade relative to the workpiece in a direction of the cutting edge when the blade is in the intermediate position; and
a moveable blade guide displaceable between a first position where the blade guide lies within the cutting arc to engage an inner surface of the continuous blade and a second position where the moveable blade guide disengages the inner surface of the continuous blade; the moveable blade guide being displaceable in a direction opposite the cutting direction, the movable blade guide having an arcuate guide surface that matches the inner surface of the cutting arc.

15. The sample cutter of claim 14 further comprising a sample defined by movement of the cutting edge through the workpiece from the first position to the second position, and translation of cutting edge along the displacement assembly between the first position and the second position, wherein the sample has a first end and a second end separated by an elongate center section.

16. The sample cutter of claim 15, wherein the moveable blade guide is biased toward the first position, and wherein the first position is perpendicular to the inner surface of the blade.

17. A sample cutter comprising:
a continuous blade having a cutting edge defining a cutting direction; a base block enclosing a portion of the blade with a remainder of the blade extending outward of the base block to form a cutting arc; the blade block being pivotally mounted to rotate the blade;
a moveable blade guide displaceable between a first position where the blade guide lies within the cutting arc to engage an inner surface of the continuous blade and a second position where the moveable blade guide disengages the inner surface of the continuous blade; the moveable blade guide being displaceable in a direction opposite the cutting direction, the movable blade guide having an arcuate guide surface that matches the inner surface of the cutting arc.

* * * * *